United States Patent [19]

Brandely et al.

[11] Patent Number: 5,204,094
[45] Date of Patent: Apr. 20, 1993

[54] TREATMENT OF PNEUMOTHORAX

[75] Inventors: Maud Brandely, Paris; Christian Boutin, Marseille, both of France

[73] Assignee: Roussel Uclaf, France

[21] Appl. No.: 822,180

[22] Filed: Jan. 16, 1992

[51] Int. Cl.⁵ ............................................. A61K 37/02
[52] U.S. Cl. ................................................. 424/85.2
[58] Field of Search ................... 424/85.2, 85.4, 85.5, 424/85.6, 85.7; 530/350, 351

[56] References Cited

U.S. PATENT DOCUMENTS 4,904,467 2/1990 Schwulera ........................... 530/351
4,944,941 7/1990 Ammann .............................. 424/85.5

Primary Examiner—Jeffrey E. Russel
Assistant Examiner—P. L. Touzeau
Attorney, Agent, or Firm—Bierman and Muserlian

[57] ABSTRACT

A method of treating pneumothoraxes in warm-blooded animals comprising administering to warm-blooded animals an amount of polypeptide having human interleukin 2 activity sufficient to treat pneumothoraxes.

8 Claims, No Drawings

TREATMENT OF PNEUMOTHORAX

STATE OF THE ART

IL2 which is a lymphokine produced by activated T lymphocytes, has an immunomodulating activity and an anti-tumoral activity described for example by Fletcher et al (Lymphokine Research, Vol 6 (1987), pp 47-57), activities which include in particular the ability to initiate the proliferation of T lymphocytes and the induction of the cytotoxicity of NK (natural killer) cells and LAK (lymphokine activated killer) cells. The numerous pharmacological studies which have shown the potential effectiveness of IL2 alone or combined with LAK cells and optionally other therapeutic agents in the therapy of cancer or infectious illnesses have been reviewed by Winkelhake et al. (Pharmacol. Reviews, 1990, Vol 42, pp 1-28).

The use of IL2 as an anti-cancer or anti-infectious agent in patients has been demonstrated and the clinical results described have shown the effectiveness of the administration of IL2 either alone at high dosage, or combined with LAK cells and optionally with other therapeutic agents, in certain types of cancers or infectious illnesses.

Other pertinent prior art includes U.S. patent application Ser. No. 384,986 filed Jul. 24, 198, now abandoned, and the Extra Pharmacopedia, 29th Edition (1989), No. 16854-S, p. 632-633.

OBJECTS OF THE INVENTION

It is an object of the invention to provide a novel method of treating pneumothorax.

This and other objects and advantages of the invention will become obvious.

THE INVENTION

The novel method of the invention for treating pneumothoraxes in warm-blooded animals, including humans, comprises administering to warm-blooded animals an amount of a polypeptide having human interleukin 2 activity sufficient to treat pneumothoraxes.

Now the Applicant has just obtained, in an unexpected manner, results showing that IL2 has an activity in the treatment of pneumothorax.

Pneumothorax is an affection characterized by an eruption of air in the pleural cavity, that is to say in the space between the parietal and visceral pleurae. Essentially, it includes spontaneous pneumothoraxes, possibly complicating the evolution of an underlying pneumopathy or a bronchopathy and induced pneumothoraxes, for example a pneumothorax complicating the effects of a thoracoscopy, pneumothoraxes of traumatic origin or those arising as complications from pleural or pulmonary biopsies. These different types of pneumothorax frequently become chronic.

Among the spontaneous pneumothoraxes which are the most frequent cause of chronic pneumothoraxes, there can be identified benign pneumothoraxes which generally occur on a previously healthy lung and which often have a tendency to reoccur and symptomatic pneumothoraxes of localized or generalized bronchopulmonary disorders.

An established sole treatment does not exist, notably in the case of spontaneous pneumothorax, particularly due to variability in the estimation of the risk of spontaneous relapse which is comprised between 20 and 50% and which then generally increases with each episode.

According to a series of 72 patients of which the published results have focused on more than 1,100 cases of spontaneous pneumothorax, the treatment capable of re-establishing pleural adhesion (or symphysis) which are described with an associated relapse rate comprise: bed rest (relapse rate 28%), drainage (relapse rate 21%), administration of tetracycline (relapse rate 20.8%), spraying of a fibrin glue (relapse rate 15.2%), introduction of talcum powder into the pleural cavity (relapse rate 6%) and thoracotomy (relapse rate 1 5%). Among these treatments, the introduction of talcum powder has a theoretical risk of carcinogenicity in the case of a prolonged or repeated treatment. Consequently, thoracotomy remains the reference treatment given its low relapse rate, but it is sometimes associated with complications, for example infections and to a certain morbidity rate.

The invention relates therefore to the use of a polypeptide having the activity of human interleukin 2 for the preparation of a pharmaceutical composition intended for the treatment of pneumothorax. By polypeptide having the activity of human IL2, natural human IL2, recombinant human IL2, that is to say that obtained by recombinant DNA technology, such as that described by Taniguchi et al. Nature, 1983, Vol 302, pp 305-310 or in European Patent NO. 91,539, is meant alleles or derivatives of these products as described for example by Ju et al, J. Biol. Chem., 1987, Vol 262, pp 5723-5731.

The pneumothoraxes to which the invention relates include spontaneous pneumothoraxes and pneumothoraxes caused by a traumatism or an invasive act, diagnosed by radiography of the thorax. Preferably, the use is characterized in that the pneumothorax is a chronic pneumothorax. The chronic pneumothorax to which the invention relates is either a spontaneous pneumothorax such as a benign spontaneous pneumothorax, notably a recurring spontaneous pneumothorax or a symptomatic spontaneous pneumothorax, for example chronic pneumopathies or bronchopathies, possibly diagnosed during routine thoracic radiography in a patient having various previous histories which are often serious, or an induced pneumothorax. In all cases, the chronic character is established for example by the persistence of frothing after ten days of pleural drainage of a detachment after this same period.

Described hereafter is the use of human IL2 in the treatment of 4 patients suffering from chronic pneumothorax, the effectiveness of which is shown by the obtention of a stable complete pleural symphysis.

A particular subject of the invention is the use of a polypeptide having the activity of human IL2 which is a pure recombinant IL2 such as recombinant human IL2, alleles or derivatives of this latter, as described above, for which purification techniques known to one skilled in the art are used, which allow to preparation of pure products.

More preferred is the use as IL2 as a non-glycosylated IL2 used is notably that having the natural IL2 sequence of 133 amino acids with optimally a supplementary N-terminal methionine, the 3 cysteines of which in position 58, 105 and 125 are in the reduced form and showing a biological activity comparable to that of oxidized IL2 having the same sequence comprising a disulfide bridge in position 58-105. This IL2 in reduced form is described in the European Patent Application EP 0,353,150. By reduced form is meant that the cysteine residues which the IL2 contains have a free sulfydryl group, the determination of which is made, for example, by spectrophotometry with dithiodipyridine as thiol reagent.

The biological activity is determined by measurement of the proliferation of leucemic cell lines of IL2 dependent mice CTLL-2, with a colorimetric test using tetrazolium salt (Mossmann, Immunol. Meth, 1983, Vol 65, p 55–63). The specific activity of the recombinant IL2's used in the invention is at least equal to $0.5 \times 10^7$ U BRMP/mg, preferably $1 \times 10^7$ U BRMP/mg. The IL2 unit of activity is defined as the quantity which produces 50% of the maximum response in the test. A "Biological Response Modifier Program (BRMP) REFERENCE AGENT HUMAN Il2 (jurkat)" sample, provided by the National Cancer Institute (NCI) is used as a standard.

Especially preferred is the use of IL2 administered by intrapleurally at a dose of $0.2 \times 10^6$ U to $3 \times 10^6$ U by injection and more specially the IL2 is administered at a dose of 0.5 to $1 \times 10^6$ U. Preferably, the IL2 is administered in a repeated manner at least once, preferably at least 3 times, at an interval of at least 1 day.

The administered dose, the frequency of injection and the duration of treatment vary as a function of the state of the patient and particularly the obtention of pleural symphysis and absence of immediate relapse of pneumothorax.

The IL2 is preferably lyophilized in a dropping bottle containing 0.05 to 2 mg of active ingredient and is reconstituted with distilled water for injection. The solution obtained is immediately diluted using a solute, for example 5% glucose for administration by intrapleural perfusion.

In a preferred use of the invention, the IL2 is the reduced recombinant IL2 above, an example of pharmaceutical preparation of which is given further on, the daily dose is approximately $1 \times 10^6$ U by slow intrapleural perfusion which is repeated at an interval of at least 1 day, preferably at least 3 times, until complete symphysis is obtained. The total dose administered to the patient is a quantity of IL2 less than 1 mg, which is more than 10 times lower than the quantities of IL2 usually administered in the treatment for example of cancers.

In the following examples, there are described several preferred embodiments to illustrate the invention. However, it is to be understood that the invention is not intended to be limited to the specific embodiments.

EXAMPLE 1

Pharmaceutical Composition for Perfusion

A preparation for injection by intravenous route by perfusion was prepared with the forumula:

| reduced IL2 | 0.5 mg |
|---|---|
| citric acid | 5.0 mg |
| mannitol | 50.0 mg |
| sterile water | 1 ml |
| 5% glucose | 50 ml |

EXAMPLE 2

Clinical Study in the Treatment of Pneumothorax

The study included 4 patients having a radiologically diagnosed chronic pneumothorax: patients A, C and D were suffering from recurring spontaneous pneumothorax and patient B was suffering from accidental pneumothorax, for which pleural drainage for at least 9 days, optionally in a repeated fashion over a period of up to 2 months, had been carried out with pulmonary radiography follow-up that has shown the failure of symphysis or recurrence of pneumothorax. As drainage proved to be ineffective, treatment with IL2 was initiated.

The IL2 compositions prepared for the invention permitted injection of IL2 at low doses which were optionally increased from 200,000 units to 1.2 million units (U) per day and which were repeated at intervals of at least 1 day, according to the response observed, by slow perfusion for example comprised between 1 and 4 hours through one, optionally two, intrapleural drainage tubes. The preparation of Example 1 was used following the protocols described above. The results were assessed on the cessation of frothing and the disappearance of gaseous effusion on radiography of the thorax.

Patient A

The 13 year-old patient was a mucoviscidosis carrier and had a pneumothorax with detachment of the lung over the entire periphery, which occurred during a coughing attack during a bronchial infection:

| Duration of previous drainage | | Dose of IL2 (U/day) | Response observed with radiography |
|---|---|---|---|
| 2 months | D1 | 200,000 | |
| | D3 | 400,000 | |
| | D4 | | partial symphysis |
| | D7 | 200,000 | total symphysis |

The pneumothorax had not reoccurred after 2 months of monitoring.

Patient B

The 22 year-old patient was affected by pulmonary fibrosis for which the carrying out of a pulmonary biopsy, with diagnostic aim, had led to the appearance of pneumothorax:

| Duration of previous drainage | | Dose of IL2 (U/day) | Response observed with radiography |
|---|---|---|---|
| 10 days | D1 | 500,000 | |
| | D3 | 800,000 | partial symphysis |
| | D5 | | total symphysis |

The pneumothorax had not reoccurred after 14 days of monitoring.

Patient C

The 73 year-old patient wa hospitalized for a progressive attack of angiosarcoma and pulmonary radiography which revealed a pneumothorax with detachment on the right side of the lung:

| Duration of previous drainage | | Dose of IL2 (U/day) | Response observed with radiography |
|---|---|---|---|
| 19 days | D1 | 1,000,000 | |
| | D3 | 1,000,000 | partial symphysis |
| | D6 | | total symphysis |

Patient D

The patient was 22 years old with a number of previous histories, one of which was stage IIIB Hodgkinson' disease. Pulmonary radiography had revealed a pneumothorax with partial left detachment of the lung:

| Duration of previous drainage | | Dose of IL2 (U/day) | Response observed with radiography |
| --- | --- | --- | --- |
| 11 days | D1 | 850,000 | |
| | D3 | 1,200,000 | |
| | D5 | | total symphysis |
| | D9 | | relapse with froth |
| | D11 | 1,000,000 | |
| | D16 | 1,000,000 | |
| | D17 | 1,000,000 | |
| | D18 | | total symphysis |
| | D20 | 1,000,000 | |
| | D22 | 1,000,000 | |
| | D23 | | total symphysis |
| | D24 | 1,000,000 | |
| | D27 | | total symphysis |

The results show a complete response in all the patients treated with IL2—(4/4).

Various modifications of the method of the invention may be made without departing from the spirit or scope thereof and it is to be understood that the invention is intended to be limited only as defined in the appended claims.

What we claim is:

1. A method of treating pneumothoraxes in warm-blooded animals comprising administering to warm-blooded animals an amount of a polypeptide having interleukin-2 activity sufficient to treat the symptoms of pneumothoraxes.

2. The method of claim 1 wherein the pneumothorax is a chronic pneumothorax.

3. The method of claim 1 wherein the polypeptide is a pure recombinant IL2.

4. The method of claim 3 wherein the polypeptide is a non-glycosylated recombinant IL2 in reduced form.

5. The method of claim 3 wherein the polypeptide is administered intrapleurally by injection at a dose of $0.2 \times 10^6$ U to $3 \times 10^6$ U.

6. The method of claim 5 wherein the dose is $0.5 \times 10^6$ to $1 \times 10^6$ U.

7. The method of claim 6 wherein the polypeptide is administered once a day.

8. The method of claim 6 wherein the polypeptide is administered repeatedly for at least three non-consecutive days.

* * * * *

UNITED STATES PATENT AND TRADEMARK OFFICE
CERTIFICATE OF CORRECTION

PATENT NO. : 5,204,094
DATED : April 20, 1993
INVENTOR(S) : N. BRANDELY, et al It is certified that error appears in the above-identified patent and that said Letters Patent is hereby corrected as shown below:

On the title page, after item [22] insert the following:
[30] Foreign Application priority data
    January 17, 1991
    France --- No. 91-00488

Signed and Sealed this

Eleventh Day of January, 1994

Attest:

BRUCE LEHMAN

*Attesting Officer*  *Commissioner of Patents and Trademarks*